United States Patent [19]

Ödman et al.

[11] Patent Number: 5,348,851

[45] Date of Patent: Sep. 20, 1994

[54] METHOD AND DEVICE FOR THE DETECTION OF VESSEL DILATATION COMPONENTS

[75] Inventors: Svante Ödman; Jan-Olof Karlsson, both of Linköping; Krister Axelsson, deceased, late of Linköping, all of Sweden, by Martin Axelsson, heir

[73] Assignee: Forsvarets Forskningsanstalt, Sundbyberg, Sweden

[21] Appl. No.: 834,227

[22] PCT Filed: Jun. 21, 1990

[86] PCT No.: PCT/SE90/00451

§ 371 Date: Feb. 21, 1992

§ 102(e) Date: Feb. 21, 1992

[87] PCT Pub. No.: WO90/15991

PCT Pub. Date: Dec. 27, 1990

[30] Foreign Application Priority Data

Jun. 22, 1989 [SE] Sweden .................. 8902294

[51] Int. Cl.⁵ .............. C12Q 1/00; G01N 33/48; G01N 31/00
[52] U.S. Cl. .......................... 435/4; 436/63; 436/110; 73/23.4; 73/23.41
[58] Field of Search ............ 435/4, 29, 30, 37; 436/63, 110; 73/23.4, 23.41, 23.42; 55/387

[56] References Cited

U.S. PATENT DOCUMENTS 3,430,482 3/1969 Dravnieks et al. ............. 73/23.41
3,568,411 3/1971 Dravnieks et al. ............. 55/208

Primary Examiner—Michael G. Wityshyn
Assistant Examiner—Ralph Gitomer
Attorney, Agent, or Firm—Jacobson, Price, Holman & Stern

[57] ABSTRACT

The present invention relates to a method and a device for the detection of vessel dilatation components. The invention particularly relates to the detection of explosives, such as trinitrotoluene (TNT) and nitroglycerin. A biological detector is used, and precontracted blood vessels or parts thereof function as sensor elements.

17 Claims, 2 Drawing Sheets

METHOD AND DEVICE FOR THE DETECTION OF VESSEL DILATATION COMPONENTS

The present invention relates to a method and a device for the detection, particularly in air, of the presence of vessel dilatation components. A biological detector is used with intestinal blood vessels or parts thereof as the sensor element. The present invention can especially be used for the detection of explosives, such as trinitrotoluene (TNT) and nitroglycerin. By means of the present invention it is possible to detect TNT in as small amounts as $10^{-15}$ mol. The sensitivity for nitroglycerin is also high, even if concentrations just as low cannot be detected.

Vessel dilatation substances can be analyzed with the use of chemically advanced and expensive equipments, being however more suitable for laboratory work. There is, however, a demand for a more field-adapted analysis apparatus, which can be used at places of work. A field-adapted analysis apparatus is also required to be used when you are searching for explosives that have been placed by terrorists and for the supervision of airports and to prevent the smuggling of explosives. It is also important to be able to find mines which have been placed in order to damage the civilian population or in order to prevent the advance of military units.

The best and most reliable method up to now for a more field-adapted detection of explosives has been to use dogs. Dogs are reported to have a sensitivity of up to $10^{-15}$ mol of TNT, which corresponds to about $10^{-13}$ g, a sensitivity which very well agrees with the requirements given if you should be able to detect a mine when passing. Also other animals such as rats have been tried and found to achieve the same high sensitivity.

We have now found that the same high sensitivity, which is achieved with rats and dogs, can be obtained if instead you use a biological preparation in vitro consisting of precontracted blood vessels in the form of sections, pieces, cellular or subcellular portions thereof, and allow air comprising the vessel dilatation components, for instance explosive vapours from TNT or nitroglycerin to pass the preparation and observe the effect of the vessel dilatation component on the vessel muscle.

Thus, the effect of the explosive vapours on the blood vessel musculature can be studied. We have found that if the vessel muscle is shortened, precontracted with phenylephrine, an adrenaline-like substance, extremely small concentrations of TNT will cause relaxation of the muscle. The effect of TNT on the vessel muscle contraction can be observed at as small amounts of TNT as $10^{-15}$ mol, which is identical with the detection limit of the mine dogs for TNT. Thus, the biological detector according to the invention can register a mine which is enclosed in a metal or plastic casing just by allowing the detector to pass in the vicinity of the mine. It can very well be used to check luggage at airports, locate bombs during bomb threats and the like, i.e. the biological detector of the invention fulfils the demands for sensitivity as well as for usability in the field.

In order to be able to register the effect of the vessel dilatation component on the blood vessel musculature, you can measure directly the change in the tension force in the muscle or the muscle elongation. You can also study the effect on the enzyme which is active at the transfer of the chemical stimulation leading to vessel dilatation. This enzyme is believed to be the hemoprotein guanylate cyclase. The hemoprotein reaction can be registered optically, for instance with the use of a fibre-optical sensor.

A device according to the present invention, measuring for instance the change in the vessel muscle contraction caused by the explosive, comprises a force measuring element, to which the vessel musculature is attached. The vessel muscle is preserved in a container holding an organ bath giving nutriment and also a proper milieu for the muscle. The muscle is also attached to the bottom of the container. Gas of a suitable composition is pumped through the container. The vapour which is to be examined is also sucked or pumped into the container the same way.

The sensor elements in the form of blood vessel pieces can be stored cold and attached inside expendable packages provided with holds for force measuring elements and counterholdings. During the analysis the blood vessel piece used in the apparatus can be exchanged for new blood vessel pieces by just a single manipulation.

The blood vessels used in accordance with the invention are preferably taken from newly slaughtered mammals, such as cows and pigs, but also from reptiles, such as snakes. If vessels from reptiles are being used, the organ bath in the form of a physiological buffer solution must not be kept at $+37°$ C. but can be of the same temperature as the environment. Intestinal blood vessels can, for instance, be used.

BRIEF DESCRIPTION OF THE DRAWINGS

The invention will now be described in more detail in an illustrative but not delimiting purpose by means of an example, and reference is made to the attached drawings, where.

EXAMPLE

Materials and methods

Figure 1:
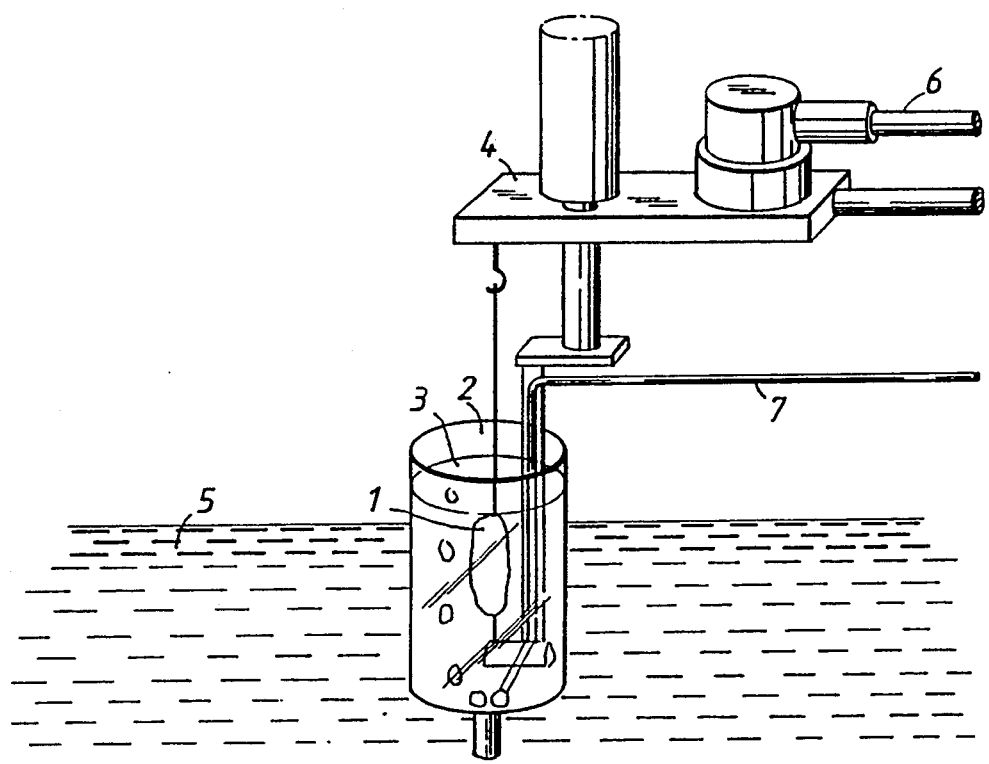
FIG. 1 shows a device according to the invention and FIG. 2(A) shows a representative registration of the effects of TNT. The blood vessel was mounted in a tension meter, and 30 $\mu$M phenylephrine (an adrenaline-like substance) was used as contracting agent.

Bovine mesenterial arteries were fetched from a local slaughter-house within 30 minutes after the slaughter. The arteries were transported to the laboratory in a thermos flask, which contained a physiological buffer solution. After the removal of surrounding fat, the arteries were opened longitudinally and then cut into pieces of about 5 mm. The pieces 1 were mounted in organ baths 2, which held physiological buffer solutions 3 and were equipped with tension sensors 4 (FIG. 1). The buffer solution was Kreb's bicarbonate buffer and was kept at 37° C. which was achieved by keeping the organ bath immersed into a water bath 5 of 37° C. The isometric tension was registered by means of Grass-amplifiers 6, which were equipped with recorders. Gas of the composition 5% carbon dioxide and 95% oxygen was pumped in through a conduit 7. After the mounting had taken place, the artery pieces were allowed to obtain equilibrium during 2 hours. Then the arteries were contracted with 3 μM phenylephrine. When a stable contraction was obtained, TNT was added in rising concentrations ($10^{-15} - 3 \times 10^{-7}$ M), and the mechanical effects from each addition were recorded.

Experimental data for the varying additions of TNT were adapted to the logistical function:

$$E = E_{max} \times A^q / (A^q + EC_{50}{}^q)$$

by means of a non-linear regression analysis utilizing a computer and a digital plotter. E, $E_{max}$ and A are the observed effect, the maximum effect and the concentration of the agonist (in this case TNT) respectively. $EC_{50}$ is the concentration which gives half of the maximum effect and q is the slope of the curve. The results are presented as arithmetric average values ±S.E.M. (standard error of means).

Results and Discussion

Figure 2A:
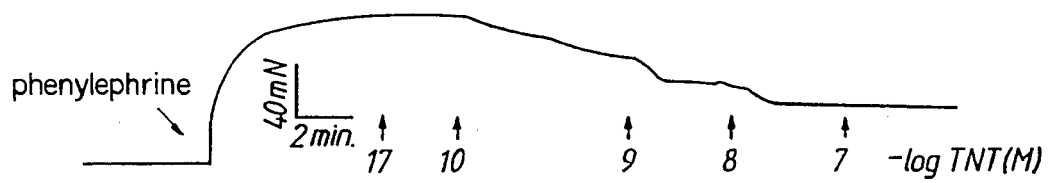
Figure 2B:
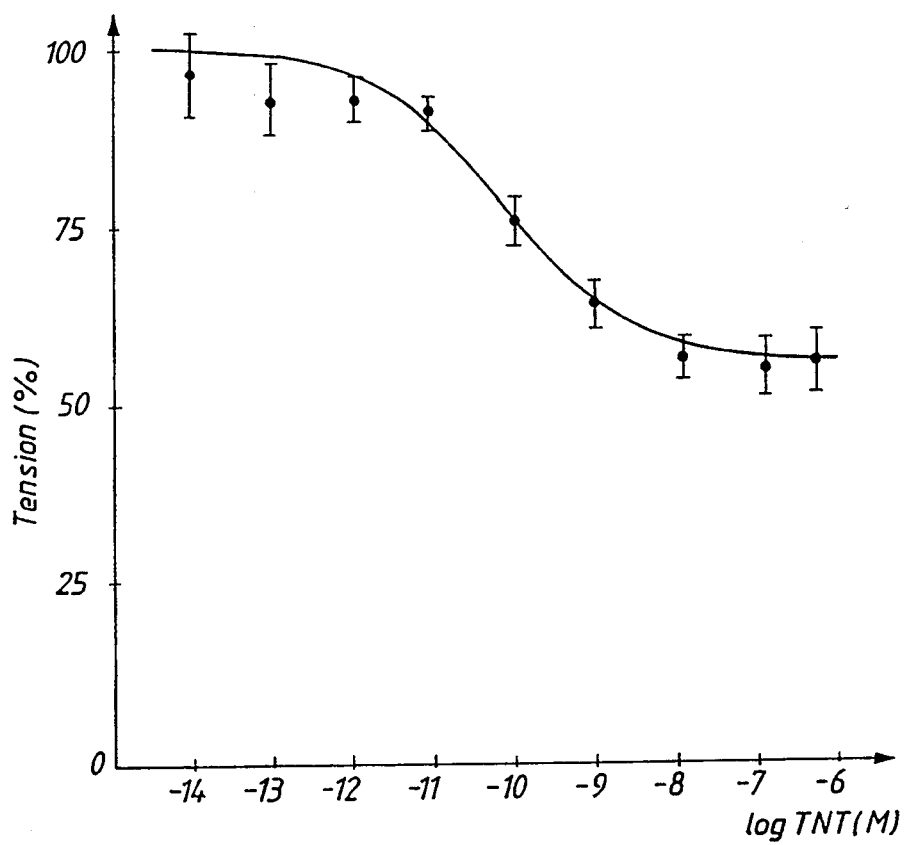
FIG. 2 shows (B) a concentration-effect curve for TNT. The effect (the y-axis) gives the percentage tension change induced by different concentrations of TNT (0% tension=before the addition of phenylephrine; 100%=after the addition of 30 $\mu$M phenylephrine). The vertical lines give the S.E.M. (n=15).

It was found that TNT in extremely small amounts relax precontracted bovine mesenterial arteries (FIG. 2). The lowest concentration of TNT giving a reproducible effect corresponds to the theoretical detection limit of mine dogs. In occasional cases, effects of even smaller amounts of TNT could be observed.

We claim:

1. A method for determining the activity of vessel dilatation components, said method comprising:
   causing contraction of a blood vessel preparation by exposing it to an alpha-adrenoceptor agonist,
   exposing the contracted blood vessel preparation to a vessel dilatation component, and
   determining the relaxation effect on the blood vessel preparation caused by the exposure to the vessel dilatation component.

2. A method according to claim 1, wherein a muscle tension in the blood vessel preparation is measured by a tension meter before and after the exposing step, a change in tension being an indication of the activity.

3. A method according to claim 1, wherein a length of the blood vessel preparation is measured before and after the exposure, the blood vessel preparation elongation being an indication of the activity.

4. A method according to claim 1, wherein the relaxation effect on the blood vessel preparation is determined before and after the exposure of the contracted blood vessel preparation to the vessel dilatation components by measuring optically by a fiber-optical sensor the contents of hemoprotein in the blood vessel preparation.

5. A method according to claim 1, wherein the blood vessel preparation is taken from an artery and selected from the group consisting of section, cellular and subcellular portion thereof.

6. A method according to claim 1, wherein the blood vessel preparation is taken from a vein and selected from the group consisting of section, cellular and subcellular portion thereof.

7. A method according to claim 1, wherein the blood vessel preparation is made from blood vessels taken from mammals.

8. A method according to claim 7, wherein the blood vessel preparation is made from blood vessels from bovine specimen.

9. A method according to claim 1, wherein the blood vessel preparation is made from blood vessels taken from reptiles.

10. A method according to claim 1, wherein the alpha-adrenoceptor agonist is adrenaline.

11. A method according to claim 1, wherein the alpha-adrenoceptor agonist is phenylephrine.

12. A method according to claim 1, wherein the contracted blood vessel preparation is exposed to vessel dilatation vapors evolved to the environment from a nitrogenous explosive.

13. A method according to claim 12, wherein the contracted blood vessel preparation is exposed to vapors vessel dilatation from evolved to the environment trinitrotoluene. (TNT).

14. A method according to claim 12, wherein the contracted blood vessel preparation is exposed to the vapors from nitroglycerin.

15. A device for determination of activity of vessel dilatation components, comprising:
   a blood vessel preparation which has been precontracted by an alpha-adrenoceptor agonist;
   an organ bath holding a physiological buffer solution suitable for the preparation;
   a water bath into which the organ bath is immersed and having a temperature suitable for the preparation;
   a conduit for gas supply to the preparation;
   a tension meter;
   means for the attachment of the preparation to the organ bath and to the tension meter; and
   a plotting device for recording changes measured by the tension meter caused by relaxation of the blood vessel.

16. A device according to claim 15, wherein vapors from trinitrotoluene (TNT) are supplied by said conduit to the precontracted blood vessel preparation.

17. A device according to claim 15, wherein vapors from nitroglycerin are supplied by said conduit to the precontracted blood vessel preparation.

* * * * *